US012111518B2

(12) United States Patent
Hones et al.

(10) Patent No.: US 12,111,518 B2
(45) Date of Patent: Oct. 8, 2024

(54) OPHTHALMIC LENSES WITH DYNAMIC OPTICAL PROPERTIES FOR REDUCING DEVELOPMENT OF MYOPIA

(71) Applicant: SIGHTGLASS VISION, INC., Palo Alto, CA (US)

(72) Inventors: Peter Hones, Menlo Park, CA (US); Thomas W. Chalberg, Jr., Menlo Park, CA (US)

(73) Assignee: SightGlass Vision, Inc., Dallas, TX (US)

(*) Notice: Subject to any disclaimer, the term of this patent is extended or adjusted under 35 U.S.C. 154(b) by 370 days.

(21) Appl. No.: 17/605,935

(22) PCT Filed: Apr. 22, 2020

(86) PCT No.: PCT/US2020/029273
§ 371 (c)(1),
(2) Date: Oct. 22, 2021

(87) PCT Pub. No.: WO2020/219518
PCT Pub. Date: Oct. 29, 2020

(65) Prior Publication Data
US 2022/0252904 A1    Aug. 11, 2022

Related U.S. Application Data

(60) Provisional application No. 62/837,688, filed on Apr. 23, 2019.

(51) Int. Cl.
| G02C 7/08 | (2006.01) |
| A61B 3/04 | (2006.01) |
| G02C 7/04 | (2006.01) |

(52) U.S. Cl.
CPC ............ *G02C 7/083* (2013.01); *A61B 3/04* (2013.01); *G02C 7/04* (2013.01); *G02C 2202/24* (2013.01)

(58) Field of Classification Search
CPC .......... G02C 7/083; G02C 7/04; G02C 7/085; G02C 2202/24; G02C 11/10; A61B 3/04
(Continued)

(56) References Cited

U.S. PATENT DOCUMENTS

| 149,270 A | 3/1847 | Watson |
| 338,003 A | 3/1886 | Ward |

(Continued)

FOREIGN PATENT DOCUMENTS

| AU | 2005289302 | 4/2006 |
| CN | 1909860 | 2/2007 |

(Continued)

OTHER PUBLICATIONS

Ahern "Biochemical, reagents kits offer scientists good return on investment," The Scientist, Jul. 1995, 9(15):20.
(Continued)

*Primary Examiner* — William R Alexander
(74) *Attorney, Agent, or Firm* — Fish & Richardson P.C.

(57) ABSTRACT

An ophthalmic lens includes a first region corresponding to a first area of an optical surface of the ophthalmic lens and a second region corresponding to a second area of the optical surface of the ophthalmic lens different from the first area The second region has an optically-switchable component switchable between a first optical state and a second optical state different from the first optical state. In the first optical state the second region partially scatters or defocuses light incident on the second area.

24 Claims, 9 Drawing Sheets

(58) Field of Classification Search
USPC .................................................. 351/159.39
See application file for complete search history.

(56) References Cited

U.S. PATENT DOCUMENTS

| | | |
|---|---|---|
| 506,983 A | 10/1893 | Diemmer et al. |
| 712,466 A | 10/1902 | Taylor |
| 3,507,566 A | 4/1970 | Knapp |
| 4,194,814 A | 3/1980 | Fischer et al. |
| 4,338,003 A | 7/1982 | Adrian |
| 4,704,016 A | 11/1987 | de Carle |
| 4,710,327 A | 12/1987 | Neefe |
| 4,909,818 A | 3/1990 | Jones |
| 5,034,100 A | 7/1991 | Sides |
| 5,260,727 A | 11/1993 | Oksman et al. |
| 5,585,968 A | 12/1996 | Guhman et al. |
| 5,800,992 A | 9/1998 | Fodor et al. |
| 5,837,461 A | 11/1998 | Neitz |
| 5,867,247 A | 2/1999 | Martin et al. |
| 5,905,561 A | 5/1999 | Lee et al. |
| 5,926,250 A | 7/1999 | Mukaiyama et al. |
| 6,129,435 A | 10/2000 | Reichow et al. |
| 6,149,270 A | 11/2000 | Hayashi |
| 6,343,861 B1 | 2/2002 | Kris et al. |
| 6,582,908 B2 | 6/2003 | Fodor et al. |
| 6,706,867 B1 | 3/2004 | Lorenz |
| 6,712,466 B2 | 3/2004 | Dreher |
| 6,712,467 B1 | 3/2004 | Kitani |
| 6,754,299 B2 | 6/2004 | Patch |
| 6,997,554 B2 | 2/2006 | Nakada et al. |
| 7,025,460 B2 | 4/2006 | Smith et al. |
| 7,218,375 B2 | 5/2007 | Galstian et al. |
| 7,506,983 B2 | 3/2009 | To et al. |
| 7,604,351 B2 | 10/2009 | Fukuma et al. |
| 7,665,842 B2 | 2/2010 | Ho et al. |
| 7,766,482 B2 | 8/2010 | Smith et al. |
| 7,862,171 B2 | 1/2011 | Varnas et al. |
| 7,901,075 B2 | 3/2011 | Rooney et al. |
| 7,992,997 B2 | 8/2011 | Varnas |
| 7,997,727 B2 | 8/2011 | Ho et al. |
| 8,000,022 B2 | 8/2011 | Niederer |
| 8,052,278 B2 | 11/2011 | Bovet et al. |
| 8,057,034 B2 | 11/2011 | Ho et al. |
| 8,079,702 B2 | 12/2011 | Ballet et al. |
| 8,115,792 B2 | 2/2012 | Petsch et al. |
| 8,162,477 B2 | 4/2012 | Carimalo et al. |
| 8,240,847 B2 | 8/2012 | Holden et al. |
| RE43,851 E | 12/2012 | To et al. |
| 8,342,684 B2 | 1/2013 | Ho et al. |
| 8,500,278 B2 | 8/2013 | Lo et al. |
| 8,540,365 B2 | 9/2013 | Varnas |
| 8,558,985 B2 | 10/2013 | Nystrom et al. |
| 8,684,520 B2 | 4/2014 | Lindacher et al. |
| 8,690,319 B2 | 4/2014 | Menezes |
| 8,807,747 B2 | 8/2014 | Guilloux et al. |
| RE45,147 E | 9/2014 | To et al. |
| 8,833,936 B2 | 9/2014 | Varnas |
| 8,926,092 B2 | 1/2015 | Weeber |
| 8,931,897 B2 | 1/2015 | Holden et al. |
| 8,950,860 B2 | 2/2015 | Tse et al. |
| 8,951,729 B2 | 2/2015 | Neitz et al. |
| 8,992,010 B2 | 3/2015 | Ho et al. |
| 8,998,408 B2 | 4/2015 | Wei et al. |
| 9,360,683 B2 | 6/2016 | Buehren |
| 9,417,463 B2 | 8/2016 | Brennan et al. |
| 9,423,633 B2 | 8/2016 | Ho et al. |
| 9,547,182 B2 | 1/2017 | Collins et al. |
| 9,594,259 B2 | 3/2017 | Brennan et al. |
| 9,625,739 B2 | 4/2017 | Brennan et al. |
| 9,709,819 B2 | 7/2017 | Lippens et al. |
| 9,720,253 B2 | 8/2017 | Neitz et al. |
| 9,733,494 B2 | 8/2017 | Brennan et al. |
| 9,746,693 B2 | 8/2017 | Peloux et al. |
| 9,829,722 B2 | 11/2017 | Tse et al. |
| 10,012,849 B2 | 7/2018 | Collins et al. |
| RE47,006 E | 8/2018 | To et al. |
| 10,042,091 B2 | 8/2018 | Kildishev et al. |
| 10,061,143 B2 | 8/2018 | Brennan et al. |
| 10,156,737 B2 | 12/2018 | Martinez et al. |
| 10,203,522 B2 | 2/2019 | Bakaraju et al. |
| 10,231,897 B2 | 3/2019 | Tse et al. |
| 10,247,964 B2 | 4/2019 | Sankaridurg et al. |
| 10,302,962 B2 | 5/2019 | Neitz et al. |
| 10,429,670 B2 | 10/2019 | Newman |
| 10,571,717 B2 | 2/2020 | Neitz et al. |
| 10,787,707 B2 | 9/2020 | Neitz et al. |
| 10,795,181 B2 | 10/2020 | Neitz et al. |
| 10,884,264 B2 | 1/2021 | Hones et al. |
| 11,048,102 B2 | 6/2021 | Neitz |
| 2002/0140900 A1 | 10/2002 | Streibig |
| 2003/0082576 A1 | 5/2003 | Jones et al. |
| 2004/0110179 A1 | 6/2004 | Shuber |
| 2004/0150787 A1 | 8/2004 | Niculas |
| 2004/0156021 A1 | 8/2004 | Blum et al. |
| 2005/0208555 A1 | 9/2005 | Raimond |
| 2006/0082729 A1 | 4/2006 | To et al. |
| 2006/0235428 A1 | 10/2006 | Silvestrini |
| 2006/0285071 A1 | 12/2006 | Erickson et al. |
| 2006/0291020 A1 | 12/2006 | Knox et al. |
| 2007/0026167 A1 | 2/2007 | Bourdelais et al. |
| 2007/0115431 A1 | 5/2007 | Smith et al. |
| 2007/0247588 A1 | 10/2007 | Cano |
| 2007/0296916 A1 | 12/2007 | Holden et al. |
| 2008/0030675 A1 | 2/2008 | Dillon |
| 2008/0055541 A1 | 3/2008 | Coulter et al. |
| 2008/0084534 A1 | 4/2008 | Lindacher et al. |
| 2008/0151183 A1 | 6/2008 | Altmann |
| 2008/0174732 A1 | 7/2008 | Blum et al. |
| 2008/0221674 A1 | 9/2008 | Blum et al. |
| 2008/0309882 A1 | 12/2008 | Thom et al. |
| 2009/0059168 A1 | 3/2009 | Miller et al. |
| 2009/0115962 A1 | 5/2009 | Bovet et al. |
| 2009/0204207 A1 | 8/2009 | Blum et al. |
| 2010/0021889 A1 | 1/2010 | Juo |
| 2010/0091240 A1 | 4/2010 | Drobe et al. |
| 2010/0149488 A1 | 6/2010 | Lo et al. |
| 2011/0051079 A1 | 3/2011 | Martinez et al. |
| 2011/0194195 A1 | 8/2011 | Zalevsky et al. |
| 2011/0313058 A1 | 12/2011 | Neitz et al. |
| 2012/0014977 A1 | 1/2012 | Furihata |
| 2012/0062836 A1 | 3/2012 | Tse et al. |
| 2012/0182520 A1 | 7/2012 | Neitz et al. |
| 2013/0053425 A1 | 2/2013 | To et al. |
| 2013/0103147 A1 | 4/2013 | Christie et al. |
| 2013/0107206 A1 | 5/2013 | Slater |
| 2014/0080900 A1 | 3/2014 | Neitz et al. |
| 2014/0111763 A1 | 4/2014 | Griffin |
| 2015/0036102 A1 | 2/2015 | Ghosh et al. |
| 2015/0109574 A1 | 4/2015 | Tse et al. |
| 2015/0111782 A1 | 4/2015 | Neitz et al. |
| 2015/0160477 A1 | 6/2015 | Dai et al. |
| 2015/0316788 A1 | 11/2015 | Holden et al. |
| 2015/0331255 A1 | 11/2015 | Sankaridurg et al. |
| 2016/0026000 A1 | 1/2016 | Kester |
| 2016/0143801 A1 | 5/2016 | Lam et al. |
| 2016/0377884 A1 | 12/2016 | Lau et al. |
| 2017/0115509 A1 | 4/2017 | Brennan et al. |
| 2017/0131567 A1 | 5/2017 | To et al. |
| 2017/0168320 A1 | 6/2017 | Tsubota et al. |
| 2017/0184875 A1 | 6/2017 | Newman |
| 2017/0189168 A1 | 7/2017 | Zickler et al. |
| 2017/0192252 A1 | 7/2017 | Brennan et al. |
| 2017/0276963 A1 | 9/2017 | Brennan et al. |
| 2017/0292160 A1 | 10/2017 | Neitz et al. |
| 2017/0336653 A1 | 11/2017 | Bakaraju |
| 2018/0112268 A1 | 4/2018 | Neitz et al. |
| 2018/0153684 A1 | 6/2018 | Heugten et al. |
| 2018/0246354 A1 | 8/2018 | Popovich et al. |
| 2018/0275425 A1 | 9/2018 | Collins et al. |
| 2018/0275427 A1 | 9/2018 | Lau et al. |
| 2019/0033619 A1 | 1/2019 | Neitz et al. |
| 2019/0235279 A1 | 8/2019 | Hones et al. |
| 2019/0302477 A1 | 10/2019 | Neitz et al. |
| 2020/0073147 A1 | 3/2020 | Bakaraju et al. |

(56) References Cited

U.S. PATENT DOCUMENTS

| | | |
|---|---|---|
| 2020/0089023 A1 | 3/2020 | Zhou et al. |
| 2020/0271955 A1 | 8/2020 | Neitz et al. |
| 2020/0393699 A1 | 12/2020 | Neitz |
| 2021/0165244 A1 | 6/2021 | Hones et al. |
| 2021/0341753 A1 | 11/2021 | Neitz |
| 2022/0035179 A1 | 2/2022 | Rappon et al. |

FOREIGN PATENT DOCUMENTS

| | | |
|---|---|---|
| CN | 2924572 | 7/2007 |
| CN | 101198434 | 6/2008 |
| CN | 101273882 | 10/2008 |
| CN | 101595420 | 12/2009 |
| CN | 101730500 | 6/2010 |
| CN | 102238927 | 11/2011 |
| CN | 103097940 | 5/2013 |
| CN | 103959138 | 7/2014 |
| CN | 104094164 | 10/2014 |
| CN | 104094165 | 10/2014 |
| CN | 104678572 | 6/2015 |
| CN | 105378545 | 3/2016 |
| CN | 102892380 | 10/2016 |
| EP | 0457612 | 11/1991 |
| EP | 1799166 | 6/2007 |
| EP | 2131721 | 12/2009 |
| EP | 2616876 | 7/2013 |
| EP | 2962155 | 1/2016 |
| EP | 2548533 | 2/2018 |
| EP | 3667401 | 6/2020 |
| HK | 1210838 | 5/2016 |
| JP | S5829627 | 2/1983 |
| JP | H05328258 | 12/1993 |
| JP | 2004514921 | 5/2004 |
| JP | 2008040497 | 2/2008 |
| JP | 2008514318 | 5/2008 |
| JP | 2011-515157 | 5/2011 |
| JP | 4891249 | 3/2012 |
| JP | 2012513252 | 6/2012 |
| JP | 2013537317 | 9/2013 |
| JP | 2017510851 | 4/2017 |
| JP | 2019529968 | 10/2019 |
| KR | 100686551 | 2/2007 |
| KR | 100840845 | 6/2008 |
| TW | 279510 | 6/1996 |
| TW | 201211618 | 3/2012 |
| TW | 201307942 | 2/2013 |
| TW | I530727 | 4/2016 |
| TW | I559044 | 11/2016 |
| TW | I561885 | 12/2016 |
| WO | WO1986/006846 | 11/1986 |
| WO | WO1997/031286 | 8/1997 |
| WO | WO1999/066366 | 12/1999 |
| WO | WO2000/052516 | 9/2000 |
| WO | WO2002/031585 | 4/2002 |
| WO | WO2006/034652 | 4/2006 |
| WO | WO2006/113149 | 10/2006 |
| WO | WO2007/082268 | 7/2007 |
| WO | WO2007/132834 | 11/2007 |
| WO | WO2008/026674 | 3/2008 |
| WO | WO2008/045847 | 4/2008 |
| WO | WO2008/059178 | 5/2008 |
| WO | WO2008/083418 | 7/2008 |
| WO | WO 2009136667 | 11/2009 |
| WO | WO2010/019397 | 2/2010 |
| WO | WO2010/075319 | 7/2010 |
| WO | WO2010/088644 | 8/2010 |
| WO | WO2011/031948 | 3/2011 |
| WO | WO2012/034265 | 3/2012 |
| WO | WO2012/097213 | 7/2012 |
| WO | WO2013/015743 | 1/2013 |
| WO | WO2013/082545 | 6/2013 |
| WO | WO2013/134825 | 9/2013 |
| WO | WO2014/194444 | 12/2014 |
| WO | WO2015/055322 | 4/2015 |
| WO | WO2015/147758 | 10/2015 |
| WO | WO2015/186723 | 12/2015 |
| WO | WO2016/138512 | 9/2016 |
| WO | WO2017/005608 | 1/2017 |
| WO | WO2017/178430 | 10/2017 |
| WO | WO2018/026697 | 2/2018 |
| WO | WO2018/076057 | 5/2018 |
| WO | WO2018/208724 | 11/2018 |
| WO | WO2018/219828 | 12/2018 |
| WO | WO2019/073676 | 4/2019 |
| WO | WO2019/166653 | 9/2019 |
| WO | WO2020/138127 | 7/2020 |

OTHER PUBLICATIONS

Anstice et al., "Effect of dual-focus soft contact lens wear on axial myopia progression in children." Ophthalmology, 2011, 1152-1161.

Applied Biosystems—Product Bulletin—Automated DNA Sequencing [online] "ABI PRISM® BigDyeTM Primer Sequencing Kit," 2000, retrieved from URL <tools.thermofisher.com/content/sfs/brochures/cms_040730.pdf>>, 4 pages.

Brennan et al., "Commonly held beliefs about myopia that lack a robust evidence base, " Eye & Contact Lens, Jul. 2019, 45(4):215-225.

Carkeet et al., "Repeatability of IOLMaster Biometry in Children, Optometry and Vision Science", Nov. 2004, 81(11) : 829-834.

Carroll et al., "Cone photoreceptor mosaic disruption associated with Cys203Arg mutation in the M-cone opsin," Proceedings of the National Academy of Sciences of the United States of America, 2009, 106(49):20948-20953.

Carroll et al., "Estimates of L:M cone ratio from ERG flicker photometry and genetics," Journal of Vision, 2002, 2(8):531-542.

Carroll et al., "Flicker-photometric electroretinogram estimates of L:M cone photoreceptor ratio in men with photopigment spectra derived from genetics," Journal of the Optical Society of America A, 2000, 17(3):499-509.

Carroll, et al., "Functional photoreceptor loss revealed with adaptive optics: An alternate cause of color blindness," Proceedings of the National Academy of Sciences of the United States of America, 2004, 101(22):8461-8466.

Cheng et al., "Effect of Bifocal and Prismatic Bifocal Spectacles on Myopia Progression in Children: Three-Year Results of a Randomized Clinical Trial", JAMA Ophthalmology, Mar. 2014, 132(3):258-264.

Cheng et al., "Soft contact lenses with positive spherical aberration for myopia control," Optometry and Vision Science, Apr. 2016, 93(4):353-366.

Crognale et al., "Characterization of a novel form of X-linked incomplete achromatopsia", Visual Neuroscience, 2004, 21(3):197-203.

Davidoff, "Cone opsin gene variants in color blindness and other vision disorders," 2015, Retrieved from URL <https://digital.lib.washington.edu/researchworks/bitstream/handle/1773/33578/Davidoff_washington_0250E_15133.pdf?sequence=1&isAllowed=y>, 132 pages.

Drummond-Borg, et al., "Molecular patterns of X chromosome-linked color vision genes among 134 men of European ancestry," Proceedings of the National Academy of Sciences of the United States of America, Feb. 1989, 86:983-987.

Gardner et al., "Three Different Cone Opsin Gene Array Mutational Mechanisms with Genotype-Phenotype Correlation and Functional Investigation of Cone Opsin Variants" Human Mutation, 2014, 35(11):1354-1362.

GeneCards [online], "GeneCard for the OPNIMW gene", retrieved on Apr. 6, 2020, retrieved from URL <genecards.org/cgi-bin/carddisp_pl?gene=OPNIMW>, 27 pages.

Greenwald et al., "Role of a Dual Splicing and Amino Acid Code in Myopia, Cone Dysfunction and Cone Dystrophy Associated with L/M Opsin Interchange Mutations," Translation Vision Science & Technology, May 2017, 6(3): 19 pages.

Gunther et al., "Individual differences in chromatic (red/green) contrast sensitivity are constrained by the relative number of L-versus M-cones in the eye," Vision Research, May 2002, 42(11):1367-1378.

(56) References Cited

OTHER PUBLICATIONS

Gwiazda et al., "A Randomized Clinical Trial of Progressive Addition Lenses versus Single Vision Lenses on the Progression of Myopia in Children", Investigative Ophthalmology & Visual Science, Apr. 2003, 44:1492-1500.
Hahner et al., "Strategies for SNP genotyping by mass spectrometry," International Congress Series, Jan. 2003. 1239: 11-16.
Halushka et al., "Patterns of single-nucleotide polymorphisms in candidate genes for blood-pressure homeostasis", Nat Genet, 1999, 239-247.
Hattersley et al., "What makes a good genetic association study?" The Lancet, Oct. 2005, 366(9493):1315-1323.
Hirschhorn et al., "A comprehensive review of genetic association studies," Genetics in Medicine, 2002, 4(2):45-61.
Hofer et al., "Organization of the Human Trichromatic Cone Mosaic," Journal of Neuroscience, Oct. 19, 2005, 25(42):9669-9679.
International Preliminary Report on Patentability in International Appln. No. PCT/US2020/029273, dated Nov. 4, 2020, 11 pages.
International Search Report and Written Opinion in International Appln. No. PCT/US2020/029273, dated Aug. 28, 2020, 5 pages.
Jones et al., "The Prevalence and Impact of High Myopia," Eye & Contact Lens, May 2012, 38(3):188-96.
Kuchenbecker et al., "Topography of the long- to middle-wavelength sensitive cone ratio in the human retina assessed with a wide-field color multifocal electroretinogram," Vis Neurosci, May-Jun. 2008, 25(3):301-6.
Lucentini, "Gene association studies typically wrong: reproducible gene-disease associations are few and far between," The Scientist, 2004, 18(24):20, 4 pages.
McClements et al., "Variations in Opsin Coding Sequences Cause X-Linked Cone Dysfunction Syndrome, with Myopia and Dichromacy," Investigative Ophthalmology & Visual Science, 2013, 54(2):1361-1369.
McMahon et al., "The L:M cone ratio in males of African descent with normal color vision," Journal of Vision, 2008, 8(2):1-9.
Michaelides et al., "The PROMI Mutation p.R373C Causes an Autosomal Dominant Bull's Eye Maculopathy Associated with Rod, Rod-Cone, and Macular Dystrophy," Sep. 2010, 51:4771-4780.
Michaelides et al., "X-Linked Cone Dysfunction Syndrome with Myopia and Protanopia," Ophthalmology, Aug. 2005, 112(8): 1448-1454.
Mizrahi-Meissonnier et al., "Variable Retinal Phenotypes Caused by Mutations in the X-Linked Photopigment Gene Array," Investigative Ophthalmology & Visual Science, Aug. 2010, (51):3884-3892.
Montana State University [online], "Optical System Design—Optical Transfer Function (OTF) Modulation Transfer Function (MTF)," 2001, retrieved from URL <https://www.montana.edu/jshaw/documents/18%20EELE582_S15_OTFMTF.pdf>, 18 pages.
Mummidi et al., "Evolution of Human and Non-human Primate CC Chemokine Receptor 5 Gene and mRNA,Potential Roles for Haplotype and mRNA Diversity, Differential Haplotype-Specific Transcriptional Activity, and Altered Transcription Factor Binding To Polymorphic Nucleotides in the Pathogenesis of HIV-1 and Simian Immunodeficiency Virus*210," Journal of Biological Chemistry, 2000, 275(25):18946-18961.
Nathans et al., "Molecular Genetics of Human Blue Cone Monochromacy," Aug. 1989, 45(4920):831-838.
Nathans et al., "Molecular Genetics of Inherited Variation in Human Color Vision," Apr. 1986, 232(4747):203-210.
NCBI Database GenBank Accession No. NM 020061, Nov. 1, 2009, National Center for Biotechnology Information, National Library of Medicine, Bethesda, MD, USA, 7 pages.
Neitz et al., "Variety of genotypes in males diagnosed as dichromatic on a conventional clinical anomaloscope," Visual Neuroscience, 2004, 21(3):205-216.
Neitz et al., "Cone mosaic disruption caused by L/M opsin mutations in bornholm eye disease," ARVO Annual Meeting Abstract, Apr. 2011, 2 pages.
Neitz et al., "Polymorphism in the number of genes encoding long-wavelength-sensitive cone pigments among males with normal color vision," Vision Research, Sep. 1995, 35(17): 2395-2407.
Neitz et al., "A new mass screening test for color-vision deficiencies in children" Color Research & Application, 2001, 26(1): S239-S249.
Oda et al., "Analysis of L-cone/M-cone visual pigment gene arrays in females by long-range PCR," Vision Research, Mar. 2003, 43(5):489-495.
Okada et al., "Target Spatial Frequency Determines the Response to Conflicting Defocus—and Convergence—Driven Accommodative Stimuli," Feb. 2006, 46(4):475-484.
Radhakrishna et al., "The 'X-linked' severe form of myopia locus at Xq28 (MYP1): Narrowing of the critical region and exclusion of twelve known genes localized in the interval," ARVO Annual Meeting Abstract, May 2005, 1 page.
Ruiz-Pomeda et al., "MiSight Assessment Study Spain (MASS). A 2-year randomized clinical trial," Graefe's Archive for Clinical and Experimental Ophthalmology, Feb. 3, 2018, 256:1011-1021.
Sankaridurg et al., "Decrease in rate of myopia progression with a contact lens designed toreduce relative peripheral huperopia: One-year results," IOVS, Dec. 2011, 52(13):9362-9367.
Scholl et al., "Macular dystrophy with protan genotype and phenotype studied with cone type specific ERGs," Current Eye Research, 2001, 22(3):221-228.
Scholl et al., "Progressive cone dystrophy with deutan genotype and phenotype," Graefe's Arch Clin Exp Ophthalmol, 2006, 244:183-191.
Schwartz et al., "X-linked myopia: Bornholm Eye Disease," Clinical Genetics, 1990, 38(4):281-286.
Slrlounge.com [online] "Diffraction, Aperture, and Starburst Effects," dated Feb. 9, 2011, retrieved on Jan. 7, 2019, retrieved from URL <https://www.slrlounge.com/diffraction-aperture-and-starburst-effects/>, 11 pages.
Tedja et al., "Genome-wide association meta-analysis highlights light-induced signaling as a driver for refractive error," Nature Genetics, Jun. 2018, 50(6):834-848.
Twelker et al., "Children's Ocular Components and Age, Gender, and Ethnicity," Optometry and Vision Science, Aug. 2009, 86(8):918-935.
Ueyama et al., "Unique haplotype in exon 3 of cone opsin mRNA affects splicing of its precursor, leading to congenital color vision defect," Biochemical and Biophysical Research Communications, 2012, 424(1):152-157.
Verrelli et al., "Signatures of Selection and Gene Conversion Associated with Human Color Vision Variation," The American Journal of Human Genetics, 2004,75(3): 363-375.
Vitale et al., "Increased prevalence of myopia in the United States between 1971-1972 and 1999-2004," Arch Ophthalmol., Dec. 2009, 127(12):1632-1639.
Winderickx et al., "Defective colour vision associated with a missense mutation in the human green visual pigment gene," Nat Genet 1992, 251-256.
Winderickx, et al., "Haplotype diversity in the human red and green opsin genes: evidence for frequent sequence exchange in exon 3," Human Molecular Genetics, 1993, 2(9):1413-1421.
Young et al., "X-Linked High Myopia Associated With Cone Dysfunction," Arch Ophthalmol. 2004, 122(6):897-908.
Young et al., "Further refinement of the MYP2 locus for autosomal dominant high myopia by linkage disequilibrium analysis," Ophthalmic Genetics, 2001, 22:69-75.
Zhang, "Genetics of Refraction and Myopia," Progress in Molecular Biology and Translational Science, 2015, 134: 269-279.
EP Extended Search Report in European Application No. 20794295.4, dated May 19, 2022, 12 pages.
EP Supplemental Extended Search Report in European Application No. 20794295.4, dated Aug. 25, 2022, 10 pages.
Office Action in British Appln. No. GB2116510.5, dated Apr. 18, 2023, 5 pages.
Office Action in Japanese Appln. No. 2021-563096, dated Nov. 6, 2023, 8 pages (with English translation).
Office Action in Taiwanese Appln. No. 109113526, dated Oct. 13, 2023, 27 pages (with English translation).

(56) References Cited

OTHER PUBLICATIONS

Office Action in Japanese Appln. No. 2021-563096, dated Aug. 5, 2024, 10 pages (with English translation).
Office Action in Chinese Appln. No. 202080030476.3, dated Aug. 15, 2024, 16 pages (with English translation).

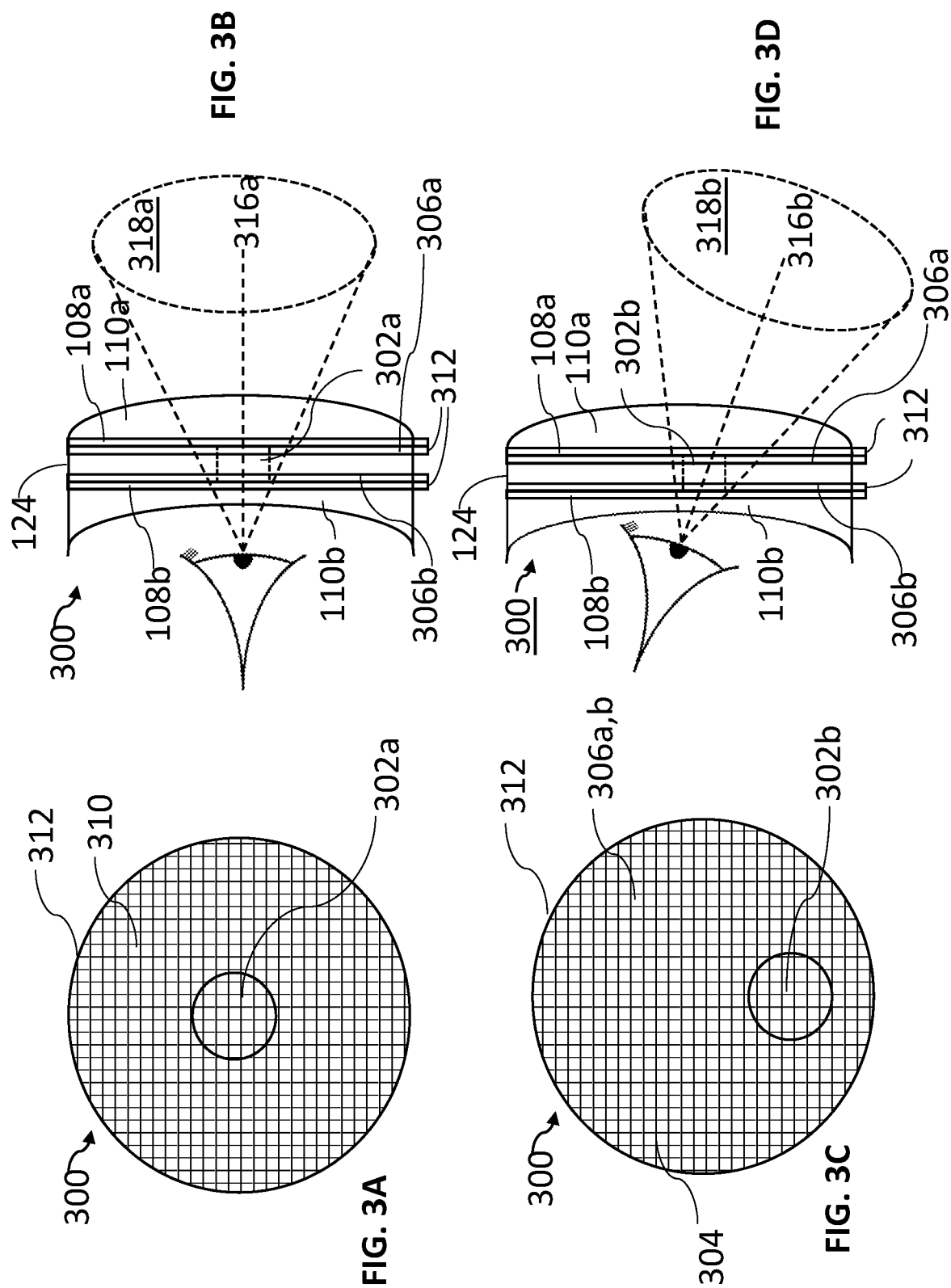

OPHTHALMIC LENSES WITH DYNAMIC OPTICAL PROPERTIES FOR REDUCING DEVELOPMENT OF MYOPIA

CROSS-REFERENCE TO RELATED APPLICATIONS

This application is a national phase entry under 35 U.S.C. 371 of PCT Application Serial No. PCT/US2020/029273, filed on Apr. 22, 2020, which claims priority to U.S. Provisional Application Ser. No. 62/837,688, filed on Apr. 23, 2019. The entirety of each of the foregoing applications are incorporated by reference.

TECHNICAL FIELD

This disclosure relates to ophthalmic lenses with dynamic optical properties and more particularly to ophthalmic lenses with dynamic optical properties for reducing development of myopia.

BACKGROUND

The eye is an optical sensor in which light from external sources is focused, by a lens, onto the surface of the retina, an array of wavelength-dependent photosensors. Each of the various shapes that the eye lens can adopt is associated with a focal length at which external light rays are optimally or near-optimally focused to produce inverted images on the surface of the retina that correspond to external images observed by the eye. The eye lens, in each of the various shapes that the eye lens can adopt, optimally or near-optimally, focuses light emitted by, or reflected from external objects that lie within a certain range of distances from the eye, and less optimally focuses, or fails to focus objects that lie outside that range of distances.

In normal-sighted individuals, the axial length of the eye, or distance from the lens to the surface of the retina, corresponds to a focal length for near-optimal focusing of distant objects. The eyes of normal-sighted individuals focus distant objects without nervous input to muscles which apply forces to alter the shape of the eye lens, a process referred to as "accommodation." Closer, nearby objects are focused, by normal individuals, as a result of accommodation.

Many people, however, suffer from eye-length-related disorders, such as myopia ("nearsightedness"). In myopic individuals, the axial length of the eye is longer than the axial length required to focus distant objects without accommodation. As a result, myopic individuals can view near objects clearly, but objects further away are blurry. While myopic individuals are generally capable of accommodation, the average distance at which they can focus objects is shorter than that for normal-sighted individuals.

Typically, infants are born hyperopic, with eye lengths shorter than needed for optimal or near-optimal focusing of distant objects without accommodation. During normal development of the eye, referred to as "emmetropization," the axial length of the eye, relative to other dimensions of the eye, increases up to a length that provides near-optimal focusing of distant objects without accommodation. Ideally, biological processes maintain the near-optimal relative eye length to eye size as the eye grows to final, adult size. However, in myopic individuals, the relative axial length of the eye to overall eye size continues to increase during development, past a length that provides near-optimal focusing of distant objects, leading to increasingly pronounced myopia.

It is believed that myopia is affected by behavioral factors as well as genetic factors. Accordingly, myopia may be mitigated by therapeutic devices which address behavioral factors. For example, therapeutic devices for treating eye-length related disorders, including myopia, are described in U.S. Pub. No. 2011/0313058A1.

SUMMARY

In general, in a first aspect, the invention features an ophthalmic lens, including: a first region corresponding to a first area of an optical surface of the ophthalmic lens; and a second region corresponding to a second area of the optical surface of the ophthalmic lens different from the first area, the second region having an optically-switchable component switchable between a first optical state and a second optical state different from the first optical state, wherein in the first optical state the second region partially scatters or defocuses light incident on the second area.

Embodiments of the ophthalmic lens can include one or more of the following features and/or features of other aspects. For example, in at least one optical state, the first area is a substantially transparent area.

The first area can have a maximum dimension (e.g., a diameter) in a range from about 2 mm to about 10 mm.

The first area can be a circular area.

The first region can include the optically-switchable component and can be switchable between a transparent optical state and a partially scattering optical state.

The second area can surround the first area.

In the second optical state, the second region can be substantially transparent (e.g., have a transparency similar to CR-39 or polycarbonate).

In the second optical state, the second region can partially scatter light incident on the second area by an amount that is different than the first optical state.

The optically-switchable component can be switchable between more than two optical states. For example, the optically-switchable component can be continuously tunable between different optical states.

The first area can intersect with an optical axis of the ophthalmic lens.

The first area can correspond with a user's foveal visual field for distance viewing.

The second area can be switchable between different optical powers. For example, the second area can be switchable between a first optical power corresponding to an optical power of the first area and a second optical power in which the second area introduces a myopic defocus to light passing through the ophthalmic lens. The second area can correspond to one or more lenslets. The second area can correspond to one or more annular regions.

The optically-switchable component can include an electro-optic material, such as a material including a liquid crystal material. In some embodiments, the electro-optic material is a polymer-dispersed liquid crystal (PDLC) material. The electro-optic material can be arranged in a layer between two transparent substrates. At least one substrate can support an electrode layer. The electrode layer can be formed from a transparent electrically-conducting material (e.g., indium tin oxide). Each of the substrates can support an electrode layer and at least one of the electrode layers can be a patterned electrode layer including a first electrode corresponding to the first region and a second electrode corresponding to the second electrode. The electrode layers can be patterned to provide a pixelated electrode structure. The electrodes can be passively addressable electrodes or actively addressable electrodes.

The lens can be a plano lens, a single vision lens, or a multivision lens.

The lens can be an eyeglass lens or a contact lens.

In general, in another aspect, the invention features a system, including: eyewear including a pair of ophthalmic lenses each switchable between at least two different optical states, wherein in a first of the two different optical states a region of one or both of the ophthalmic lenses, the system reduces a contrast of images viewed through a first region of the respective ophthalmic lens compared to images viewed through a second region of the respective ophthalmic lens; a power supply arranged to provide electrical power to the pair of ophthalmic lenses to switch each ophthalmic lens between the two different optical states; and an electronic controller in communication with the power supply and the ophthalmic lenses and programmed to control delivery of the electrical power from the power supply to each of the ophthalmic lenses.

Embodiments of the system can include one or more of the following features and/or features of other aspects. For example, the system can reduce contrast of images as viewed by a wearer of the eyewear by increasing an amount of scattering of incident light on an area of the lens corresponding to the first region.

The system can reduce contrast of images by adding light to images viewed through an area of the lens corresponding to the first region. The eyewear can include a projection display module that directs light to the user's eyes and the system adds light to images viewed through the area of the lens corresponding to the first region using the projection display module.

The system can include one or more sensors in communication with the electronic controller, at least one of the sensors being an eye-tracking sensors providing information about movement of a user's eye to the electronic controller. The electronic controller can be programmed to vary an area of the at least one ophthalmic lens corresponding to the second region in response to the information about the movement of the user's eye. The electronic controller can be programmed to vary the area corresponding to the second region so that it coincides with the user's gaze axis.

The system can include one or more sensors in communication with the electronic controller, at least one of the sensors being an environmental sensors providing information about the user's environment to the electronic controller. The environmental sensor can be a proximity sensor and the electronic controller can be programmed to vary an optical state of the ophthalmic lenses based on the information from the proximity sensor. The electronic controller can be programmed to vary an optical state of the ophthalmic lenses based on the information from the environmental sensor. The electronic controller can vary the optical state by varying a location of an area of the respective ophthalmic lens corresponding to the first region.

The ophthalmic lenses can each be switchable between more than two different optical states, each optical state corresponding to a different level of contrast reduction of images viewed through the first region of the respective ophthalmic lens.

The power supply can include a battery, such as a rechargeable battery.

The eyewear can include eyeglass frames housing the power supply and the electronic controller.

The system can include a headset comprising the eyewear, power supply, and the electronic controller. The headset can be an augmented reality (AR) headset.

In general, in a further aspect, the invention features a method for reducing contrast of images formed in a person's peripheral vision, including: varying, using an optically-switchable material in an ophthalmic lens used by the person, an amount of scattering in an area of the lens.

Implementations of the method can include one or more of the following features and/or features of other aspects. For example, the varying can include varying an area of the lens which scatters incident light and varying an area of the lens that is transparent.

The varying the area can include varying a size of the area. Varying the area can include varying a location of the area.

The amount of scattering can be varied based on a visual task of the person (e.g., reading, viewing a screen).

The amount of scattering can be varied based on the person's eye movements. The amount of scattering can be varied to align a transparent area of the lens with the person's central visual axis and align a scattering area with the person's peripheral visual field.

In general, in yet another aspect, the invention features a method for reducing contrast of images formed in a person's peripheral vision, including: using a head mounted light projection module, directing light to the person's eye so that it impinges on the person's retina at locations corresponding to the person's peripheral visual field without impinging on the person's retina at locations corresponding to the person's central visual field.

Implementations of the method can include one or more of the following features and/or features of other aspects. For example, the method can include varying the light based on the person's eye movements.

The method can include varying the light based on an ambient light level.

The method can include, by a contrast sensor behind the lens, measuring image contrast past the lens and electronic circuitry (e.g., providing a feedback loop) to keep the peripheral image contrast in about constant (e.g., varying not more than 40%, not more than 30%, not more than 20%, not more than 10%).

Among other advantages, disclosed embodiments can mitigate myopia development in people, e.g., children, while providing a visual experience that adapts to environmental and other stimuli.

BRIEF DESCRIPTION OF THE DRAWINGS

FIGS. 3A and 3B area plan view and a cross-sectional view, respectively, of an embodiment of a dynamic lens featuring pixels in a first state of operation.

FIGS. 3C and 3D are a plan view and a cross-sectional view, respectively, of the dynamic lens shown in FIGS. 3A and 3B in a second state of operation.

Like references in different figures denote like elements.

DETAILED DESCRIPTION

Figure 1A:
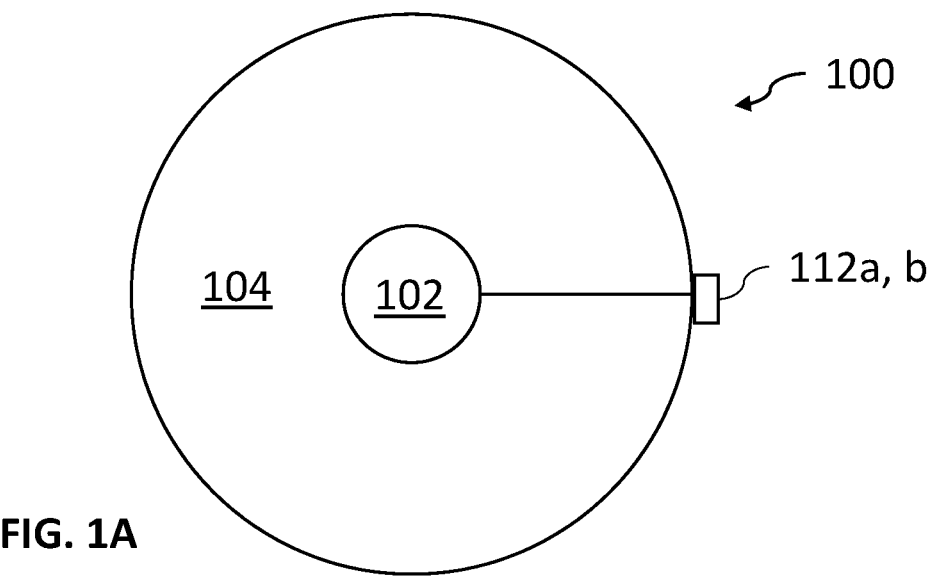
FIG. 1A is a plan view of an embodiment of a dynamic lens.
Figure 1B:
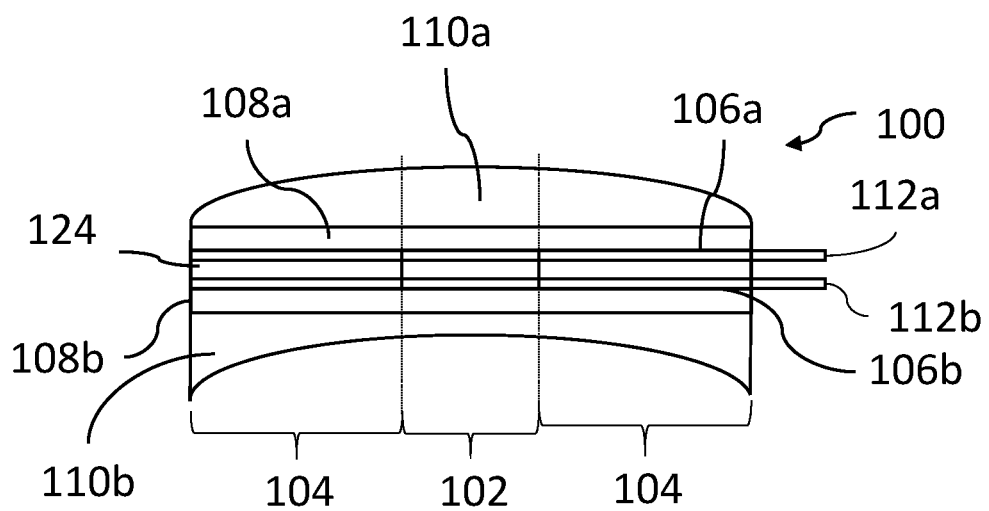
FIG. 1B is cross-sectional view of the dynamic lens shown in FIG. 1A.

Referring to FIGS. 1A and 1B, an ophthalmic lens 100 includes two regions that can be switched between different optical states independent from each other. Specifically, lens 100 includes an on-axis region 102 (i.e., the optical axis of lens 100 intersects region 102) and a peripheral region 104 surrounding on-axis region 102 that can each be switched between a state in which the region partially scatters incident light and another state in which the region is transparent. Lens 100 has a multi-layered structure composed of an electro-optic cell laminated between two layers 110a and 110b with optical power. The electro-optic cell is composed of a layer 124 of an electro-optic material sandwiched between two opposing transparent substrates 108a and 108b. Transparent electrode layers 106a and 106b are provided on facing surfaces of substrates 108a and 108b, respectively, adjacent to the electro-optic material.

Top lens layer 110a is a plano-convex layer, with a planar surface attached (e.g., via a clear adhesive) to the top surface of substrate 108a. Bottom lens layer is a plano-concave layer, with a planar surface attached to the bottom surface of substrate 108b. Accordingly, lens 100 is a meniscus lens, with the top convex surface being provided by the convex surface of top lens layer 110a and the bottom concave surface being provided by the concave surface of bottom lens layer 110b. In general, the overall optical power of lens 100 can be set to a desired value by judicious selection of the curvature of the convex and concave surfaces of these layers. For example, lens 100 can have a positive spherical optical power or a negative spherical optical power. Corrections for astigmatism and/or multifocal (e.g., progressive) lenses are also possible.

Electrode layers 106a and 106b each include two electrically isolated regions corresponding to regions 102 and 104. This allows electrically switching the electro-optic material that corresponds to each region separately from the other. Electrode connector tabs 112a and 112b extend beyond the periphery of lens 100, providing electrical connection points for connecting electrode layers 106a and 106b to a power source. An electrically-isolated line allows connection of the inner electrode regions of each electrode layer corresponding to region 102 to the power source 122 via tabs 112a and 112b. Electrode layers 106a and 106b are formed from transparent electrically-conducting materials, e.g., transparent conductive oxides such as indium tin oxide, conductive polymers, metal grids, carbon nanotubes, graphene, nanowire meshes, ultra-thin metal films).

Layer 124 is composed of an electro-optic material such as a polymer dispersed liquid crystal (PDLC), in which a liquid crystal material (e.g., a nematic LC) is dispersed or dissolved in a liquid polymer which is then solidified or cured to form a dispersion of liquid crystal droplets in a polymer matrix. Generally, the refractive index of the polymer and the refractive indices of the LC are selected so that alignment of the LC with an applied electric field results in an index-matched state between the LC droplets and the polymer, resulting in layer 124 being substantially transparent light incident on the lens. In the absence of an electric field, the orientation of the LC directors randomize and the incident light is at least partially scattered. The amount of scattering can be controlled with the applied electric field strength. Accordingly, intermediate scattering states (between transparent and a maximum scattering amount) are possible.

Other electro-optic materials can also be used. For example, in some embodiments, the electro-optic material is composed of an electrochromic material, such as tungsten oxide and/or phosphaphenalene (e.g., materials that change color depending on an applied electric field, thereby blocking and/or absorbing light).

In some embodiments, the electro-optic material of layer 124 is composed of suspended particle devices, which are typically formed from rod-like nanoparticles suspended in a liquid. The suspended particles float freely between the electrodes. In the absence of an electric field, the suspended particles are randomly organized, scattering light. In the presence of an electric potential, the suspended particles align and let light pass through.

Electrode layers 106a and 106b are formed on transparent substrates 108a and 108b are situated on top and bottom of substrates 108a and 108b can be made of glass, plastics, or other suitable transparent substrate materials. Material for the electrode layers can be formed on the substrates using a variety of processes including, e.g., coating or physical deposition processes (e.g., sputtering).

Other electrode geometries are also possible, such as interdigitated electrodes (e.g., on a single surface adjacent layer 124).

Top lens layer 110a and bottom lens layer 110b are attached to the outer surfaces of top and bottom of substrates 108a and 108b, respectively, and are also formed from transparent materials such as a glass or a transparent polymer (e.g., polycarbonate, Trivex), or other suitable transparent lens materials. A transparent adhesive can be used to bond the lens layers to the corresponding substrate surface.

In some embodiments, the outer surfaces of top and bottom lens layers 110a and 110b can include one or more layers of other materials, which can include but is not limited to a scratch-resistant coating, a mirror coating, a polarizing film, an ultraviolet coating, a scratch-resistant coating, and an anti-reflective coating.

In some embodiments, the flat surface of top and bottom lens layers provide the surface on which the electrodes are formed and a separate substrate layer is not needed.

Furthermore, while layer 124 is depicted as a homogeneous layer, i.e., the composition is the same in region 102 and region 104, other implementations are also possible. For example, layer 124 can be composed of regions having differing compositions. For example, in region 102, layer 124 can have a different composition than in region 104. For example, layer 124 can be composed of a transparent material (e.g., a transparent polymer) in region 102 and an optically-switchable material (e.g., PDLC) in region 104.

Figure 2A:
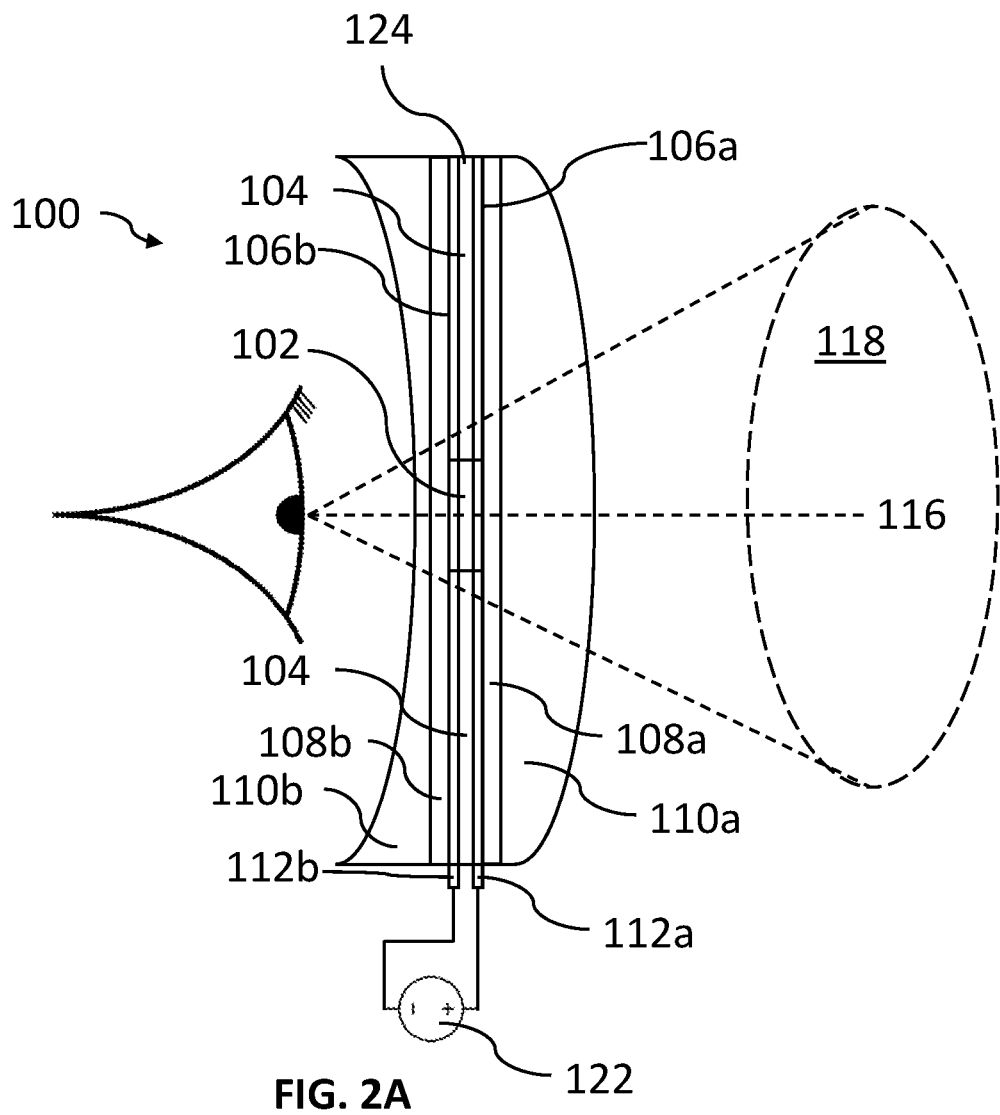
FIG. 2A is cross-sectional view of the dynamic lens shown in FIG. 1A depicting use.

Referring to FIG. 2A, region 102 and 104 are sized and positioned so that when a user of ophthalmic lens gaze axis 116 is substantially aligned with the optical axis of the lens (e.g., when the user looks right ahead through eyeglasses containing the lens), region 102 coincides with their foveal vision while region 104 coincides with their peripheral visual field 116. Thus, lens 100 can provide differing amounts of light scattering of peripheral images, controlling the amount of image contrast reduction in this region of the user's visual system.

For example, for lenses that use electro-optic materials such as PDLC's, lens 100 is switched between two or more different optical states by applying an electric field of appropriate strength across layer 124. The electric field is applied by applying a potential difference across electrode layers 106a and 106b.

While in an "off" or unenergized state (e.g., where there is no electric field across layer 124) the electro-optic material of layer 124 scatters incident light and provides reduced contrast images. When in an "on" or energized state (e.g., when an electric field of sufficient strength is applied) the electro-optic material of layer 124 becomes transparent. In some embodiments, intermediate scattering states are provided where the electrodes are energized but with a voltage having insufficient strength to eliminate all light scattering from layer 124. As the strength of the electric potential increases, layer 124 turns increasingly clearer.

Accordingly, both on-axis region 102 and peripheral region 104 can be switched between one or more scattering states and a transparent state independent of one another. In many applications, on-axis region is maintained in a transparent state while the amount of scattering provided by region 104 is varied.

The size and shape of on-axis region 102 can vary. Generally, on-axis region 102 provides the user with a viewing cone for which their visual acuity may be optimally corrected (e.g., to 20/15 or 20/20). In some embodiments, on-axis region 102 has a maximum dimension in a range from about 0.2 mm (e.g., about 0.3 mm or more, 0.4 mm or more, 0.5 mm or more, 0.6 mm or more, 0.7 mm or more, 0.8 mm or more, 0.9 mm or more) to about 1.5 cm (e.g., about 1.4 cm or less, about 1.3 cm or less, about 1.2 cm or less, about 1.1 cm or less, about 1 cm or less). On-axis region 102 can be circular (as illustrated in FIG. 1A) or non-circular (e.g., elliptical, polygonal, or irregular).

On-axis region 102 can subtend a solid angle of about 20 degrees or less (e.g., about 15 degrees or less, about 12 degrees or less, about 10 degrees or less, about 9 degrees or less, about 8 degrees or less, about 7 degrees or less, about 6 degrees or less, about 5 degrees or less, about 4 degrees or less, about 3 degrees or less) in the user's field of vision 118. The solid angles subtended in the horizontal and vertical viewing planes may be the same or different.

Figure 2B:
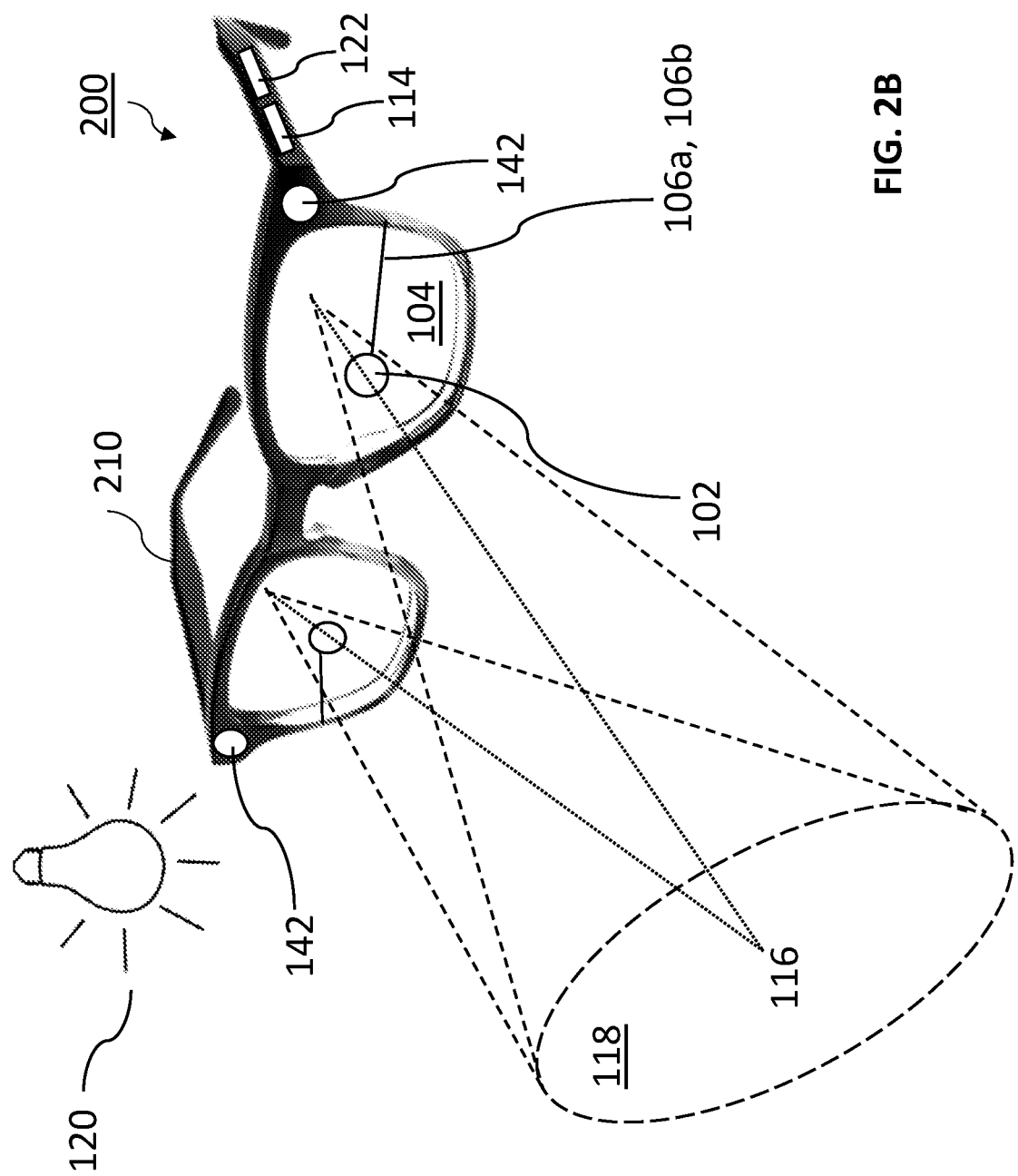
FIG. 2B is a perspective view of a pair of eyeglasses incorporating a pair of the dynamic lenses shown in FIGS. 1A and 1B.

Region 104 corresponds with the user's peripheral vision. Peripheral region 104 can extend to the edge of the lens (as shown in FIG. 1A) or can extend to less than the perimeter of the lens. In general, where region 104 does not extend to the edge of the lens, it can have a variety of shapes, e.g., circular, elliptical, polygonal, or other shape. Generally, region 104 is sufficiently large to provide reduced contrast of the user's peripheral vision over a substantial part of the user's visual field, even when not looking directly through on-axis region 102. Peripheral region 104 can have a diameter (or maximum dimension, for non-circular areas) of 30 mm or more (e.g., 40 mm or more, 50 mm or more, 60 mm or more, 70 mm or more, 80 mm or more e.g., 100 mm or less, 90 mm or less, 80 mm or less, 70 mm or less, 60 mm or less). Referring to FIG. 2B, a pair of eyeglasses 200 for reducing myopia progression includes two optically-switchable lenses 100 in eyeglass frames 210. Frames 210 also house sensors 142, an electronic controller 114, and a power source 112. Controller 114 provides electrical signals to the electrodes of the lenses, causing region 102 and/or 104 to switch between different optical states. In some embodiments, the eyeglasses include a user interface (e.g., an on/off switch or other manual control) with which the user can manually modify the optical properties of the lenses. For example, if the wearer engages in an activity known to cause high contrast retinal stimulation in the wearer's peripheral visual field, they can turn on or increase the amount of light scattering in region 104. Conversely, if the wearer engages in an activity that demands maximum visual acuity for the wearer's entire visual field, they can turn off scattering in region 104 so that the entire area of lenses 100 are transparent.

Sensors 142 monitor one or more aspects related to the wearer's environment and provide corresponding data to controller 114, allowing the controller to modify the optical properties of one or both of the lenses depending on information about the wearer's environment. Sensors 142 can include, for example, ambient light sensors, proximity sensors, and/or image sensors.

Generally, during operation, eyeglasses 200 detect environmental conditions corresponding to situations where the wearer is likely to be subjected to high-contrast images in their peripheral visual field and increases or decreases the amount of scattering in region 104 of each lens accordingly. For example, using images or proximity data from sensors 142, eyeglasses 200 can detect when the wearer is performing close reading work (e.g., reading a book or a newspaper, or reading content on a mobile device) and can increase the amount of scattering in regions 104 compared to, for example, when the user is not reading. Alternatively, or additionally, eyeglasses 200 can determine a low light environment, e.g., using an ambient light sensor, and can decrease the amount of light scattering in regions 104.

In some embodiments, one or more sensors in the peripheral area of the eyeglasses measure contrast behind the lens (i.e., after the light is transmitted by the lens. A feedback loop in the control unit uses this measurement to adjust the light scattering of the electro-optic cell. As a result, the peripheral contrast transmitted through the lens in the periphery may be maintained at constant level regardless of the contrast of the contrast of the image being viewed.

In embodiments, in a scattering state, the optically switchable material can provide sufficient scattering to reduce the contrast of images of objects in the wearer's peripheral vision without significantly degrading the viewer's visual acuity in this region. Here, peripheral vision refers to the field of vision outside of the field of view corresponding to region 102. Image contrast in region 104 can be reduced by 40% or more (e.g., 45% or more, 50% or more, 60% or more, 70% or, more, 80% or more) relative to an image contrast viewed through region 102. Contrast reduction may be set according to the needs of each individual case. It is believed that a typical contrast reduction would be in a range from about 50% to 55%. Contrast reductions of lower than 50% may be used for very mild cases, while subjects who are more predisposed might need a higher than 55% contrast reduction. Peripheral visual acuity can be corrected to 20/30 or better (e.g., 20/25 or better, 20/20 or better) as determined by subjective refraction, while still achieving meaningful contrast reduction.

Contrast, here, refers to the difference in luminance between two objects within the same field of view. Accordingly, contrast reduction refers to a change in this difference.

Contrast and contrast reduction may be measured in a variety of ways. In some embodiments, contrast can be measured based on a brightness difference between different portions of a standard pattern, such as a checkerboard of black and white squares, obtained through the a region of the lens in a transparent state and a region in a scattering state under controlled conditions.

Alternatively, or additionally, contrast reduction may be determined based on the optical transfer function (OTF) of the lens (see, e.g., http://www.montana.edu/jshaw/documents/18%20EELE582_S15_OTFMTF.pdf). For an OTF, contrast is specified for transmission of stimuli in which light and dark regions are sinusoidally modulated at different "spatial frequencies." These stimuli look like alternating light and dark bars with the spacing between bars varying over a range. For all optical systems the transmission of contrast is lowest for the sinusoidally varying stimuli having the highest spatial frequencies. The relationship describing the transmission of contrast for all spatial frequencies is the OTF. The OTF can be obtained by taking the Fourier transform of the point spread function. The point spread function can be obtained by imaging a point source of light through the lens on to a detector array and determining how light from a point is distributed across the detector.

In the event of conflicting measurements, the OTF is technique is preferred.

In some embodiments, eyeglasses 200 can receive information from other sources that can be used to control the optical properties of the lenses. For example, eyeglasses 200 can include a wireless transceiver (e.g., for Wi-Fi or Bluetooth data transmission) that facilities transfer of data between another device, such as a mobile phone, and controller 114. By way of example, the eyeglasses can receive information about the user's location (e.g., based on GPS or cellular tower data), the user's motion (e.g., whether the user is walking or driving), and/or the user's activity (e.g., watching video content, reading, or playing video games using the device) and increase or decrease peripheral light scattering accordingly.

While lenses 100 feature segmented electrodes that correspond to two different regions of the lens (regions 102 and 104), other implementations are possible. For example, in some embodiments, the lens can be segmented into more than two regions. For instance, region 104 can be further segmented into multiple regions (e.g., concentric regions) that can be independently varied between different optical states.

In certain embodiments, a dynamic lens can include an array of independently addressable pixels. For example, referring to FIG. 3A, an ophthalmic lens 300 includes an array of pixels 310, each being independently switchable between different optical states (e.g., transparent and scattering).

Referring to FIG. 3B, lens 300 has a similar structure to lens 100 described previously, with the exception that electrode layers 306a and 306b are patterned and constructed to provide pixel array 310. In addition, electrode connection tabs 312 provide electrical connection terminals suitable for the electrode drive scheme employed.

In general, the pixels in lens 300 can be actively or passively addressed pixels. For example, actively addressed pixels can each include integrated circuits (e.g., including one or more transistors) that control the electric field at that pixel. Passively addressed pixels can be provided by forming columns of conductors on one of the electrode layers 306a/306b, and rows of conductors on the other. Active and passive electrode addressing schemes conventionally applied to liquid crystal displays can be used.

The size of each pixel 310 can vary as desired. In some embodiment, pixels can have a maximum dimension of 1 mm or less (e.g., 0.5 mm or less, 0.3 mm or less, 0.2 mm or less, 0.1 mm or less, 0.05 mm or less).

Pixelated lenses allow not only fine spatial adjustment of the scattering properties of the lens, but also allow for varying the location and/or shape of the clear region of the lens. For example, FIGS. 3A and 3B show a region 302a at the center of the lens. The pixels corresponding to this region can be switched to a transparent state when the user looks directly through this region, as illustrated in FIG. 3B. This, the user's gaze axis 316a passes direction through region 302a, providing optimal visual acuity for the user's foveal vision. The pixels corresponding to the rest of the lens area (outside of region 302a) are switched to a scattering state. Thus, the user's peripheral visual field experience reduced contrast images due to light scattering in layer 124.

Referring to FIGS. 3C and 3D, lens 300 dynamically adjusts the optical properties of the lens in response to the user's gaze axis moving away from the center of the lens. Here, the user looks downward (e.g., when reading) and the lens responds by activating pixels in an off-axis a region 302b to provide a clear aperture that coincides with the user's adjusted gaze axis 316b. Furthermore, the lens switches pixels outside of region 302b to a scattering state, providing images of decreased contrast to the user's peripheral visual field 318b.

Eyewear incorporating lenses 300 can include eye-tracking sensors and the controller can be programmed to adjust the location of the clear aperture in response to data from the eye-tracking sensors. Generally, a variety of appropriate eye-tracking techniques can be used. For example, eyetracking can be performed by using a camera to direct view the pupil or by viewing the pupils reflection on the backside of the lens.

While the foregoing examples all feature lenses that reduce contrast of images in a user's peripheral image field by scattering incident light, other implementations are also possible. For example, it is possible to reduce contrast of an image by adding light to ambient, image-forming light. Accordingly, in some embodiments, eyewear can include a light source arranged to deliver light to the user's peripheral visual field. Such implementations include, for example, augmented reality (AR) eyewear that include, for example, a projection display system for overlaying a computer generated image in the user's visual field.

Figure 4A:
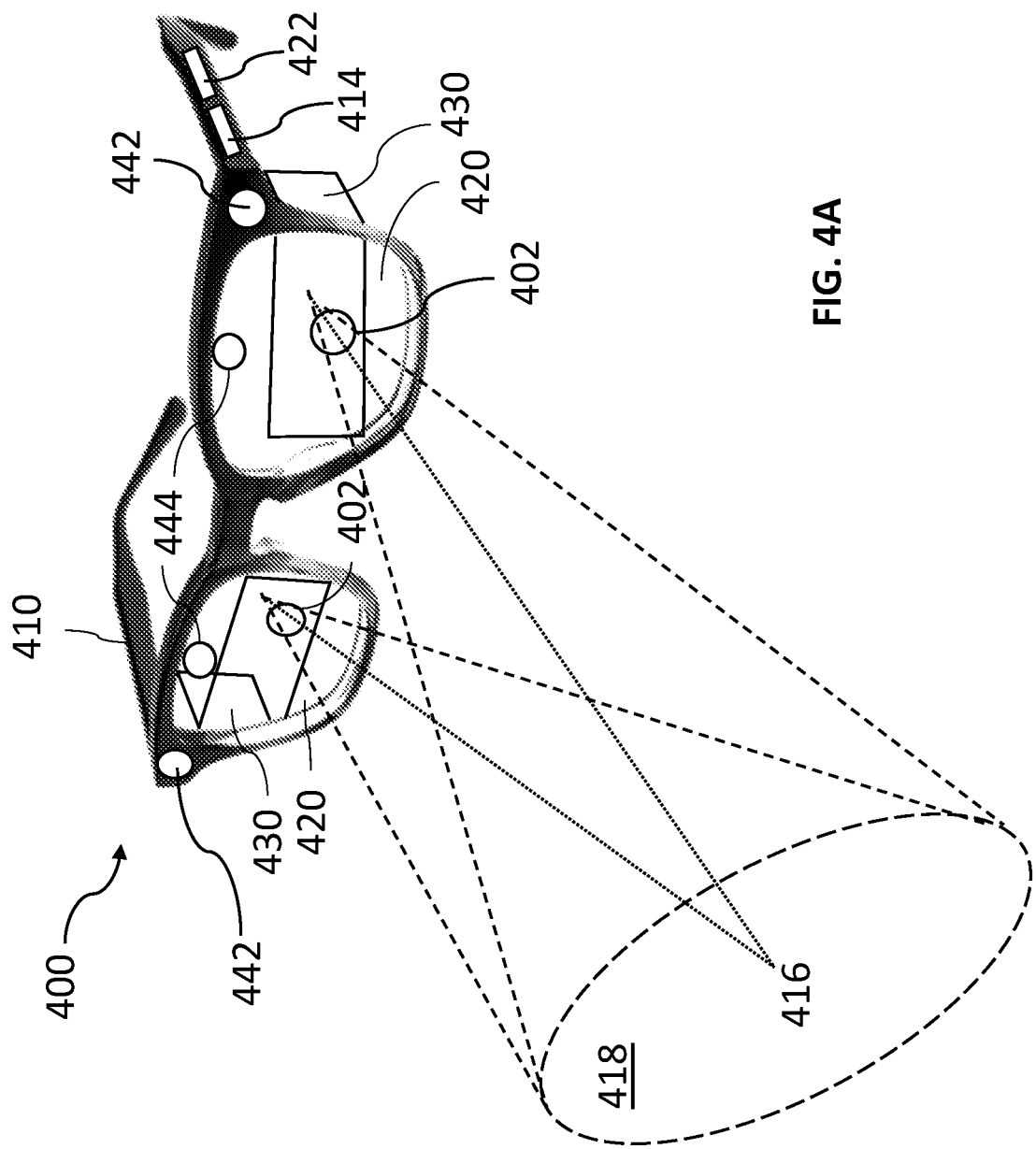
FIG. 4A is a perspective view of an augmented reality (AR) headset.

Referring to FIG. 4A, an example of an AR headset 400 includes frames 410 that hold a pair of lenses 420, which can be optically powered or unpowered. Headset 400 further includes a pair of projection display modules 430, each positioned to display images in the field of view of the wearer. The AR headset 450 includes sensors 442, eye-tracking sensors 444, a controller 414, and a power source 422.

Sensors 442 provide data to controller 414 about the user's environment. Sensors 442 can include but are not limited to ambient light sensors, image sensors (e.g., for monitoring the user's field of view), proximity sensors, accelerometers, etc. Eye-tracking sensors 444 monitor the user's pupil position and provides eye-gaze data (e.g., eye-gaze direction and duration/intensity), such as the direction of the user's eye-gaze axis 416 and field of vision 418, to controller 414.

Controller 414 receives data from sensors 442 and eye-tracking sensors 444 and controls projection display modules 430 in response to this data.

Figure 4B:
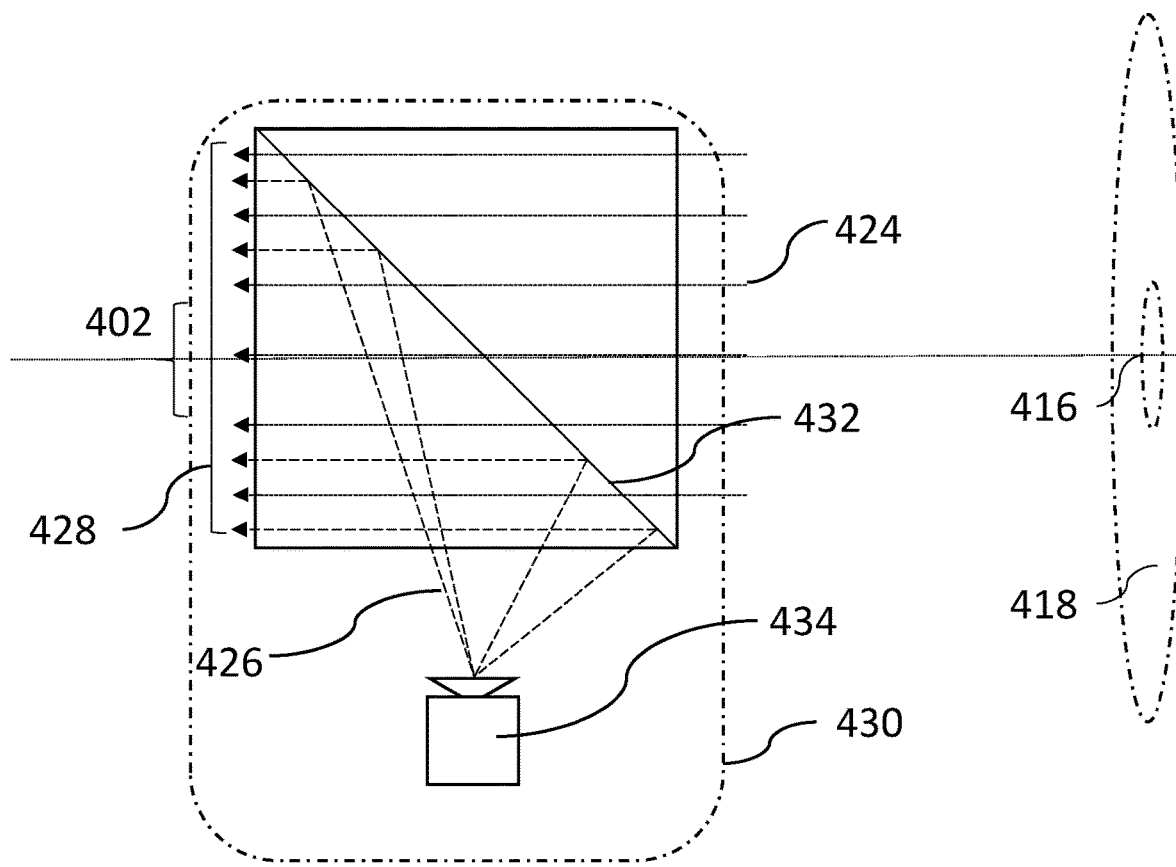
FIG. 4B is a schematic diagram of an embodiment of a projection display module used in the AR headset shown in FIG. 4A.

Referring also to FIG. 4B, projection display modules 430 include a projection display 434 and a beam splitter 432. Projection display 434 delivers light 426 to beamsplitter 432 which redirects that light into the user's field of view. Accordingly, the user visual field receives light 426 from the projection display in addition to ambient light 424, transmitted by beamsplitter 432. Headset 450 modulates light 426 so that the light from projection display 434 is limited exclusively the user's peripheral field of view 418, while delivering no light to a region 402 that corresponds to the user's central visual field 416. Using data from eye-tracking sensors 444, projection display module dynamically adjusts the modulation of the projected light field to ensure that region 402 coincides with central visual field 416. In this way, light 426 from the projection display reduces contrast of images formed in the user's peripheral visual field without affecting images in the central visual field.

Furthermore, as for embodiments discussed previously, AR headset 400 can adapt the amount of contrast reduction in the user's peripheral visual field in response to environmental changes and/or the user's actions.

Generally, projection display 434 can include a light modulator such as a MEMS mirror array or an LCD (e.g., an LCOS LCD). Projection display 434 can also include one or more light sources, such as one or more light emitting diodes (LEDs) which provide light for the light modulator. Projection display 434 can include additional components, such as imaging optical elements and/or light guides, which shape light before and/or after modulation by the light modulator in order to deliver the light to beamsplitter 432.

Alternative projection display modules can be used. For instance, rather than a beam splitter, projection display modules can include a light guiding film than delivers light from the projection display to the user's eye.

In general, while the foregoing example is of an AR headset having the form of eyeglasses, more generally a variety of AR headsets can be used. For example, AR goggles can be used. Moreover, while the electronic controller and power source and depicted as being integrated into the eyeglasses in headset 400, in some embodiments control electronics and/or power supplies can be separate from the headset and can communicate with the components of the headset using cables and/or wirelessly.

Figure 5:
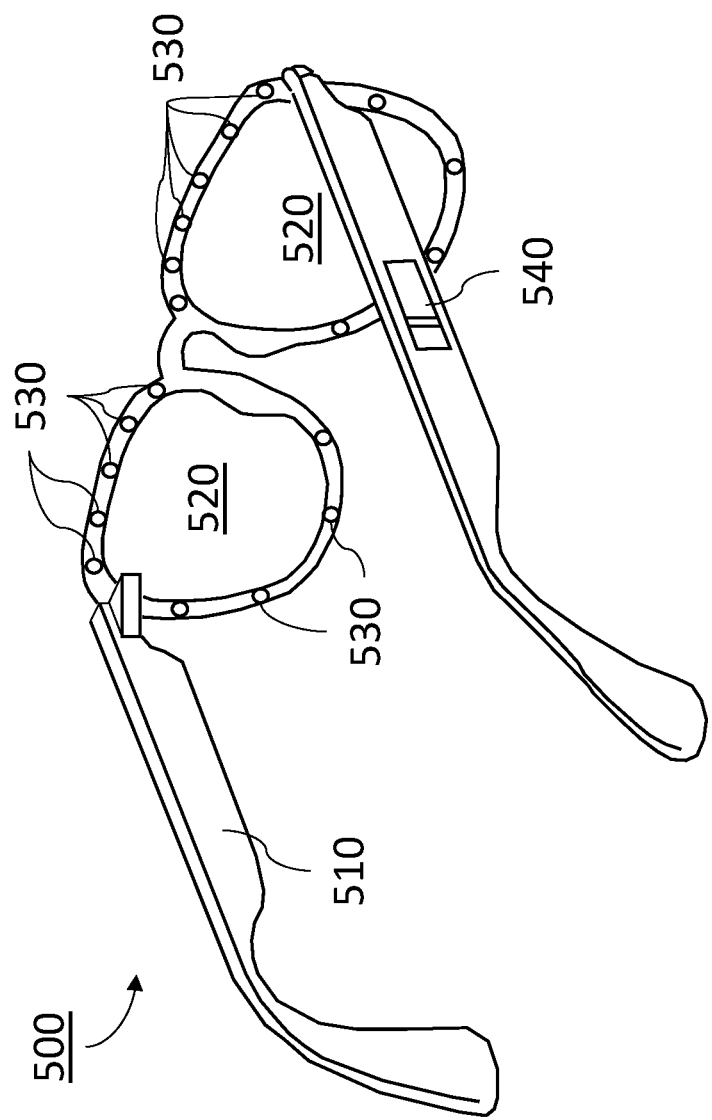
FIG. 5 is a perspective view of a pair of eyeglasses for reduced contrast in a wearer's peripheral visual field.

Other implementations are possible. For example, in some embodiments, light emitted (e.g. by one or more LEDs) mounted on the frame of the eyeglasses or headset can be used to reduced contrast in the user's visual periphery. Referring to FIG. 5, an example system implementing this is a pair of eyeglasses 500, which include frames 510, lenses 520 (e.g., Rx lenses) and LEDs 530 mounted on the rim of frames 520 facing the wearer. The wearer can manually control the brightness of the LEDs, e.g., using a slider switch 540. Alternatively, or additionally, the brightness of LEDs 530 can be controlled automatically, e.g., using a sensor and a feedback mechanism such as described above, and/or remotely, e.g., using an app on a mobile device via a wireless connection.

LEDs 530 can be include one or more optical components (e.g., one or more lenses) to direct emitted light in a specific direction, e.g., so that only contrast in the user's peripheral image field is significantly reduced while their foveal vision is largely unaffected.

In addition, while LEDs 530 are arranged to shine light directly on the wearer's retina, in some embodiment the light from the LEDs can be provided indirectly, e.g., by reflection from the back of lenses 520.

Figure 6A:
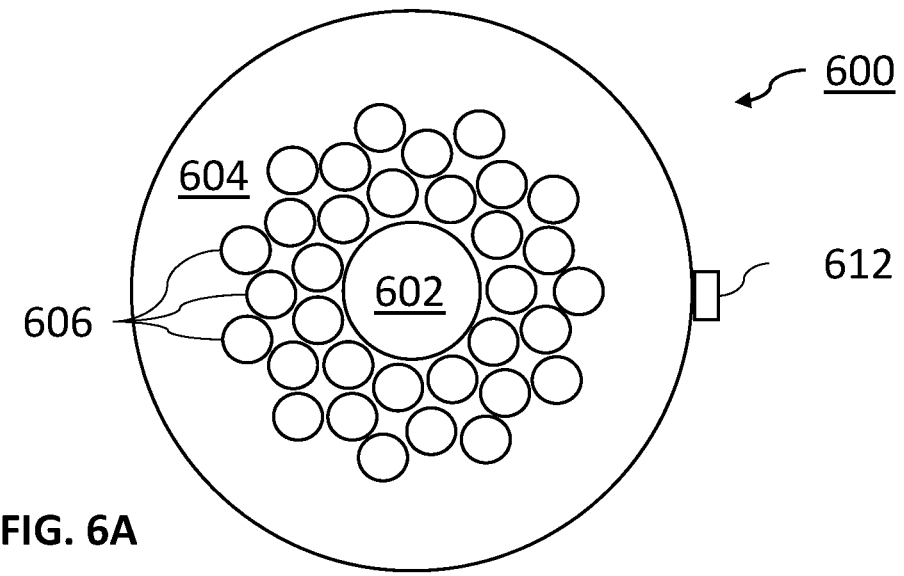
FIG. 6A is a plan view of another embodiment of a dynamic lens.

While the foregoing embodiments include implementations that reduce image contrast in images in a user's peripheral visual field by scattering incidence light, it is believed that lenses that feature an array of non-coaxial lenslets to create move the focal position of an image away from the retina (e.g., by introducing myopic defocus) can also be useful in preventing and/or slowing myopia progression. See, e.g., U.S. 2016/0377884 and U.S. 2017/0131567. Accordingly, in some embodiments, ophthalmic lenses are switchable between at least two states where, in one state, the lenses function as a conventional plano or Rx lens, providing no optical power or single vision or multifocal image correction for the user (i.e., their base state). In at least one other state, the lenses include multiple regions providing non-coaxial myopic defocus. For example, referring to FIG. 6A, an ophthalmic lens 600 includes an on-axis region 602 (e.g., the optical axis of lens 600 and/or distance viewing axis of the user intersects region 602) and a peripheral region 604 surrounding on-axis region 602 that can each be switched between a myopic defocus state and another state in which the lens provides no optical power or serves as a conventional Rx. In the myopic defocus state, region 604 features multiple lenslets 606, each having an optical power different from the rest of the lens. For example, each lenslet 606 can deliver positive foci of light in front of the user's retina sufficient to slow the rate of myopia progression.

In general, the amount of optical power provided by lenslets 606 can vary depending on the implementation. In some embodiments, in the myopic defocus state, lenslets 606 have an optical power of +0.5 D or more (e.g., +1.0 D or more, +2.0 D or more, +3.0 D or more, +4.0 D or more, +5.0 D or more, +6.0 D or more, +7.0 D or more, +8.0 D or more) greater than the base optical power of lens 600. In some embodiments, each lenslet can be switched between multiple different states from 0 D up to a maximum optical power.

The size and/or shape of lenslets 606 can also vary. For example, the lenslets can be circular with a diameter in a range from 0.4 mm to 5 mm (e.g., 0.5 mm or more, 1 mm or more, 1.5 mm or more, 2 mm or more, 4 mm or less, 3 mm or less). In some embodiments, lenslets 606 are elongated in shape (e.g., elliptical) with a largest dimension in a range from 0.4 mm to 5 mm (e.g., 0.5 mm or more, 1 mm or more, 1.5 mm or more, 2 mm or more, 4 mm or less, 3 mm or less).

In general, a variety of suitable electro-optic technologies can be used to provide the switchable lenslet array. For example, variable focus LC technology, such as described in U.S. Pat. Nos. 7,218,375 and 8,558,985, can be used.

Figure 6B:
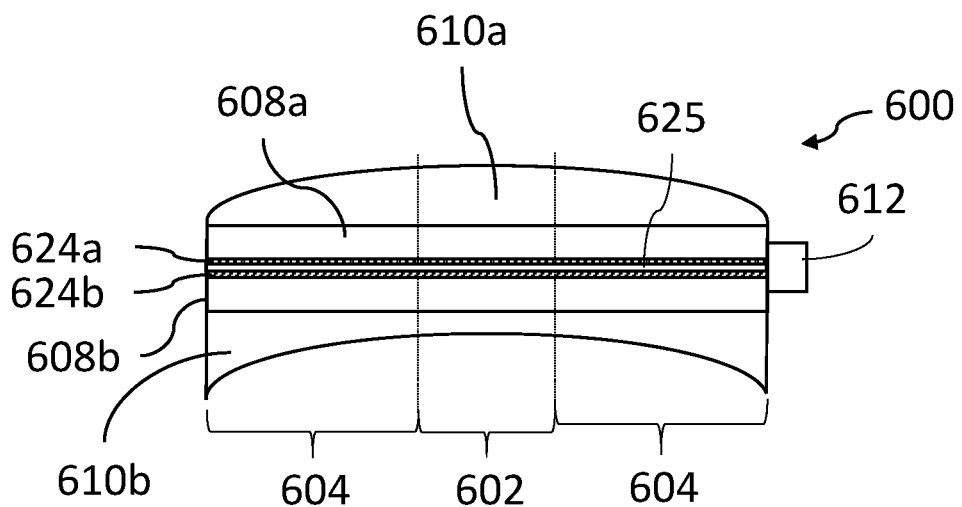
FIG. 6B is cross-sectional view of the dynamic lens shown in FIG. 6A.

By way of example, and referring to FIG. 6B, in some embodiments lens 600 has a multi-layered structure composed of an electro-optic cell laminated between two layers 610a and 610b with optical power. The electro-optic cell is composed of two layers of liquid crystal (LC) material 624a and 624b, separated by transparent separation layer 625. Layers 624a and 624b are also sandwiched between two opposing transparent substrates 108a and 108b. Transparent substrates 624a and 624b each support a transparent electrode adjacent the corresponding LC layer. Both sides of transparent separation layer 625 also support transparent electrode layers. The electrodes are electrically accessible via a tab 612 that provides electrical connections for connecting the electrode layers to a signal generator. Hence, the electro-optic cell is composed of two separately switchable LC cells each composed of a layer of LC material between two transparent electrode layers. The electrode layers can be patterned electrode layers, such as those described above, and can include actively or passively addressed pixels. Each LC cell can also include alignment layers (e.g., a buffed polymer layer) formed on top of the electrode layers. The alignment layers ensure a preferred alignment direction of the LC material adjacent the electrodes. The alignment directions of the LC material in layer 624a can be orthogonal to the alignment direction in layer 624b, ensuring a refractive index change for orthogonal polarization states propagating through the cell.

Top lens layer 610a is a plano-convex layer, with a planar surface attached (e.g., via a clear adhesive) to the top surface of substrate 608a. Bottom lens layer is a plano-concave layer, with a planar surface attached to the bottom surface of substrate 608b. Accordingly, lens 600 is a meniscus lens, with the top convex surface being provided by the convex surface of top lens layer 610a and the bottom concave surface being provided by the concave surface of bottom lens layer 610b. In general, the base optical power of lens 600 can be set to a desired value by judicious selection of the curvature of the convex and concave surfaces of these layers. For example, lens 600 can have a positive spherical optical power or a negative spherical optical power. Corrections for astigmatism and/or multifocal (e.g., progressive) lenses are also possible.

Figure 7:
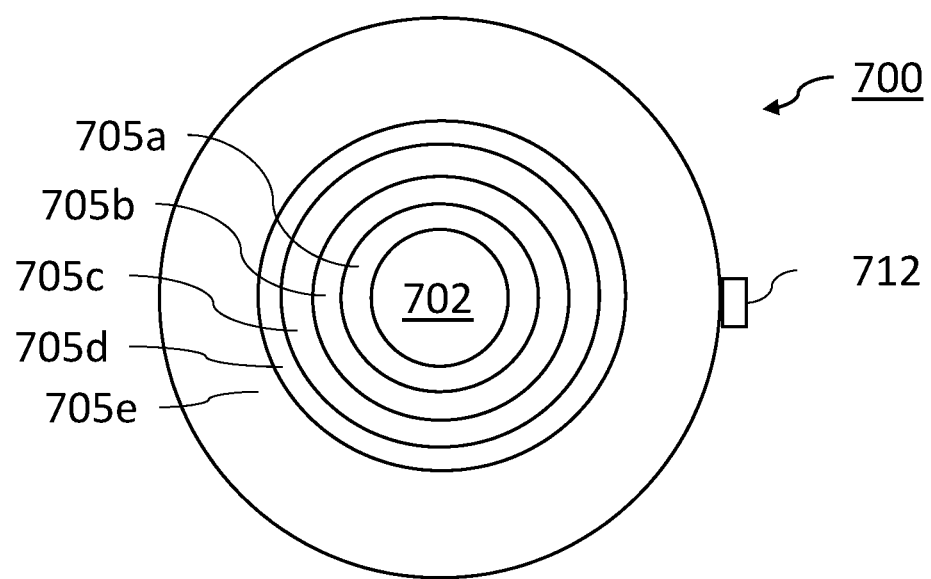
FIG. 7 is a plan view of another example of a dynamic lens.

Other switchable lens technologies can also be deployed. For example, variable focus lenses using optical fluids and/or electroactive polymers can be used. See, e.g., U.S. Pat. No. 8,000,022. Furthermore, while lens 600 features an array of lenslets, other implementations are possible. For example, more generally, the region(s) providing myopic defocus can be shaped in other shapes besides as a lenslet array. In some embodiments, the optical power of the entire peripheral region can be adjusted to have optical power sufficient to provide myopic defocus, while the central region provides optical power for distance vision. In another example, switchable annular regions of differing optical power surrounding an aperture can be employed (see, e.g., U.S. Pat. No. 7,506,983 for example structures). An example of such a lens is lens 700 shown in FIG. 7. Here, lens 700 includes an on-axis region 702 (e.g., including a correction for distance vision) and a series of annular zones 705a-705e each having differing optical power relative to the adjacent zones. The optical power of each zone can be controlled separate from the others and can be varied to have different optical powers. One or more zones can, in at least certain states, have an optical power that introduces a myopic defocus into an image.

The term "electronic controller" refers to data processing hardware and encompasses all kinds of apparatus, devices, and machines for processing data, including by way of example a programmable processor. The controller can also be, or further include, special purpose logic circuitry, e.g., an FPGA (field programmable gate array) or an ASIC (application specific integrated circuit). The controller can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

A number of embodiments have been described. Other embodiments are in the following claims.

What is claimed is:

1. An ophthalmic lens, comprising:
   a first region corresponding to a first area of an optical surface of the ophthalmic lens; and
   a second region corresponding to a second area of the optical surface of the ophthalmic lens different from the first area, the second region comprising an optically-switchable component switchable between a first optical state and a second optical state different from the first optical state, wherein in the first optical state the second region partially scatters or defocuses light incident on the second area,
   wherein in the second optical state, the second region partially scatters light incident on the second area by an amount that is different than the first optical state.

2. The ophthalmic lens of claim 1, wherein, in at least one optical state, the first area is a substantially transparent area.

3. The ophthalmic lens of claim 1, wherein the first area has a maximum dimension in a range from about 2 mm to about 10 mm.

4. The ophthalmic lens of claim 1, wherein the first area is a circular area.

5. The ophthalmic lens of claim 1, wherein the first region comprises the optically-switchable component and is switchable between a transparent optical state and a partially scattering optical state.

6. The ophthalmic lens of claim 1, wherein the second area surrounds the first area.

7. The ophthalmic lens of claim 1, wherein in the second optical state, the second region is substantially transparent.

8. The ophthalmic lens of claim 1, wherein the optically-switchable component is switchable between more than two optical states.

9. The ophthalmic lens of claim 8, wherein the optically-switchable component is continuously tunable between different optical states.

10. The ophthalmic lens of claim 1, wherein the first area intersects with an optical axis of the ophthalmic lens and/or the first area corresponds with a user's foveal visual field for distance viewing.

11. The ophthalmic lens of claim 1, wherein the optically-switchable component comprises an electro-optic material.

12. The ophthalmic lens of claim 11, wherein the electro-optic material comprises a liquid crystal material.

13. The ophthalmic lens of claim 12, wherein the electro-optic material is a polymer-dispersed liquid crystal (PDLC) material.

14. The ophthalmic lens of claim 11, wherein the electro-optic material is arranged in a layer between two transparent substrates, wherein at least one substrate supports an electrode layer.

15. The ophthalmic lens of claim 14, wherein the electrode layer is formed from a transparent electrically-conducting material.

16. The ophthalmic lens of claim 15, wherein each of the substrates support an electrode layer and at least one of the electrode layers is a patterned electrode layer comprising a first electrode corresponding to the first region and a second electrode corresponding to the second region.

17. An ophthalmic lens, comprising:
a first region corresponding to a first area of an optical surface of the ophthalmic lens; and
a second region corresponding to a second area of the optical surface of the ophthalmic lens different from the first area, the second region comprising an optically-switchable component switchable between a first optical state and a second optical state different from the first optical state, wherein in the first optical state the second region partially scatters or defocuses light incident on the second area,
wherein the second area is switchable between different optical powers and the second area is switchable between a first optical power corresponding to an optical power of the first area and a second optical power in which the second area introduces a myopic defocus to light passing through the ophthalmic lens.

18. The ophthalmic lens of claim 17, wherein the second area corresponds to one or more lenslets.

19. The ophthalmic lens of claim 17, wherein the second area corresponds to one or more annular regions.

20. A method for reducing contrast of images formed in a person's peripheral vision, comprising:
varying, using an optically-switchable material in an ophthalmic lens used by the person, an amount of scattering in an area of the lens,
wherein the amount of scattering in the area of the ophthalmic lens reduces an image contrast by 40% or more and provides a visual acuity of 20/30 or better.

21. The method of claim 20, wherein the varying comprises one or more of the following: (i) varying an area of the lens which scatters incident light and varying an area of the lens that is transparent; (ii) varying a size of the area of the lens which scatters incident light; and (iii) varying a location of the area of the lens which scatters incident light.

22. The method of claim 20, wherein the amount of scattering is varied based on a visual task of the person.

23. The method of claim 20, wherein the amount of scattering is varied based on the person's eye movements.

24. The method of claim 23, wherein the amount of scattering is varied to align a transparent area of the lens with the person's central visual axis and align a scattering area with the person's peripheral visual field.

* * * * *